United States Patent [19]

Umezawa et al.

[11] Patent Number: 4,845,082

[45] Date of Patent: Jul. 4, 1989

[54] 3'4'-DIDEOXY-3'-FLUOROKANAMYCIN B AND PRODUCTION THEREOF

[75] Inventors: Hamao Umezawa; Sumio Umezawa, both of Tokyo; Tsutomu Tsuchiya; Yoshihiko Kobayashi, both of Yokohama, all of Japan

[73] Assignee: Zaidan Hojin Biseibutsu Kagaku Kenkyu Kai, Tokyo, Japan

[21] Appl. No.: 899,100

[22] Filed: Aug. 22, 1986

[30] Foreign Application Priority Data

Aug. 29, 1985 [JP] Japan ................. 60-188525

[51] Int. Cl.$^4$ ............ A61K 31/70; C07H 15/22
[52] U.S. Cl. ..................... 514/41; 536/13.7; 536/13.8
[58] Field of Search ............ 514/41; 536/13.7, , 536/13.8

[56] References Cited

U.S. PATENT DOCUMENTS

| 4,349,666 | 9/1982 | Umezawa et al. | 536/13.8 |
| 4,634,688 | 1/1987 | Umezawa et al. | 514/41 |
| 4,661,474 | 4/1987 | Umezawa et al. | 536/13.7 |

Primary Examiner—Johnnie R. Brown
Assistant Examiner—Elli Peselev
Attorney, Agent, or Firm—Larson and Taylor

[57] ABSTRACT

New compound, 3',4'-dideoxy-3'-fluorokanamycin B is now provided, which is useful as antibacterial agent.

3',4'-Dideoxy-3'-fluorokanamycin B is prepared by a process comprising halogenating an N,O-protected derivative of 3'-deoxy-3'-fluoro-4'-O-sulfonylkanamycin B with a metal halide, reducing the resulting 4'- halogenated 3'-deoxy-3'-fluorokanamycin B derivative to convert its 4'-halo group into a hydrogen atom, and thereby to produce an N,O-protected derivative of 3',4'-dideoxy-3'-fluorokanamycin B, and removing the remaining amino-protecting groups and the remaining hydroxyl-protecting groups from the reduction product by conventional deprotecting methods.

3 Claims, 1 Drawing Sheet

FIG.1

3',4'-DIDEOXY-3'-FLUOROKANAMYCIN B AND PRODUCTION THEREOF

SUMMARY OF THE INVENTION

This invention relates to 3',4'-dideoxy-3'-fluorokanamycin B which is a new semi-synthetic aminoglycosidic antibiotic and which is a new compound exhibiting a high antibacterial activity against a variety of kanamycin-sensitive bacteria and kanamycin-resistant bacteria and is useful as antibacterial agent. This invention also relates to a pharmaceutical composition containing 3',4'-dideoxy-3'-fluorokanamycin B as the active ingredient. This invention further relates to processes for the production of the new compound of this invention.

BACKGROUND OF THE INVENTION

Various deoxy derivatives of kanamycin A, B and C are already known as the semi-synthetic aminoglycosidic antibiotics which are derived from the kanamycins. These known deoxy derivatives of the kanamycins A, B and C have usefully high antibacterial activities, but the antibacterial spectra of these known deoxy-derivatives of the kanamycins are of different ranges. These known deoxykanamycin derivatives are possible to become inactive against such new resistant strains of bacteria which will occasionally occur in future. Accordingly, it is always demanded that new, antibacterial compounds having any more excellent properties than the known antibacterial kanamycin derivatives should be produced newly and provided for uses in therapeutic treatment of bacterial infections.

We, the present inventors, had an expectation that if we would succeed in synthetizing such a new kanamycin A derivative having the 3'-hydroxyl group replaced by a fluoro group, namely 3'-fluoro-3'-deoxykanamycin A, this new kanamycin A compound should be active against some kanamycin-resistant strains of bacteria which are already known and also against some another resistant strains which will possibly occur in future.

With such expectation, we made our efforts to synthetize 3'-fluoro-3'-deoxykanamycin A, and as a result, we succeeded in synthetizing 3'-fluoro-3'-deoxykanamycin A as a semi-synthetic aminoglycosidic antibiotic, of which the process for production, physico-chemical properties and antibacterial spectra have been disclosed in Japanese patent application No. 161615/84 (filed Aug. 2, 1984 in Japan) which corresponds to U.S. patent application Ser. No. 758,819; and European patent application No. 85 401575.7.

We made our further research in attempt to synthetize a new compound, 3'-fluoro-3'-deoxykanamycin B and we succeeded in synthetizing 3'-fluoro-3'-deoxykanamycin B according to such a synthetic process as described hereinafter, wherein a known compound, 6'-N, 4'-O-carbonyl-4",6"-O-cyclohexylidene-1,2',3,3"-tetra-N-tosylkanamycin B (the compound disclosed as an N,O-protected kanamycin B derivative in Japanese patent application first publication "kokai" No. 63993/81; U.S. Pat. No. 4,349,666; and the "Nippon Kagaku Kaishi" 1982, No. 10, pages 1706–1712) was employed as a starting compound.

We have found that 3'-fluoro-3'-deoxykanamycin B has remarkable antibacterial activities against various gram-positive and gram-negative bacteria, including the resistant bacteria (Japanese patent application No. 262700/84; Japanese patent application first publication "Kokai" No. 140597/86).

However, it has been found that the new compound, 3'-fluoro-3'-deoxykanamycin B having a hydroxyl group at the 4'-position exhibits rather a low antibacterial activity against some resistant strains of bacteria capable of producing a phosphorylating enzyme and/or an adenylating enzyme which can react with the 4'-hydroxyl group. Examples of such resistant strains of bacteria are *Staphylococcus aureus* Ap 01 and *Staphylococcus epidermidis* 109.

We, therefore, had an expectation that if we would succeed in synthetizing such a new 3'-deoxy-3'-fluorokanamycin B derivative which has the 4'-hydroxyl group eliminated, namely a kanamycin B derivative identifiable as 3',4'-dideoxy-3'-fluorokanamycin B, this new 4'-deoxy-derivative of 3'-deoxy-3'-fluorokanamycin B should be active against a variety of resistant strains of bacteria of the sorts as mentioned above. As a result of our further researches, we have now succeeded in synthetizing 3',4'-dideoxy 3'-fluorokanamycin B as a new compound, and we have discovered that the new compound, 3',4'-dideoxy-3'-fluorokanamycin B now produced exhibits an enhanced antibacterial activity against a wide variety of bacteria, as compound with the 3'-fluoro-3'-deoxykanamycin B.

DETAILED DESCRIPTION OF THE INVENTION

According to a first aspect of this invention, therefore, there are provided as new compound, 3',4'-dideoxy-3'-fluorokanamycin B of the formula (I), and a pharmaceutically acceptable acid addition salt thereof.

This new compound of this invention is a semisynthetic aminoglycosidic antibiotic which is active against a variety of gram-positive and gram-negative bacteria, as well as against a variety of resistant strains of bacteria.

3',4'-Dideoxy-3'-fluorokanamycin B according to this invention may be obtained in the form of a colorless powder and is a basic substance exhibiting no definite melting point but showing the physico-chemical properties as described in the Example given hereinafter.

The new compound of the formula (I) according to this invention is usually obtained in the form of a free base, a hydrate or a carbonate thereof. The new compound of the formula (I) may, if desired, be converted into a pharmaceutically acceptable, non-toxic acid addition salt thereof in a known manner by reacting the free base form of said compound with a pharmaceutically acceptable inorganic acid such as hydrochloric acid, sulfuric acid, phosphoric acid, nitric acid and the like; or with a pharmaceutically acceptable organic acid such as acetic acid, malic acid, citric acid, ascorbic acid, methanesulfonic acid and the like.

According to a second aspect of this invention, there is also provided a pharmaceutical composition comprising the compound of the formula (I), namely 3',4'-dideoxy-3'-fluorokanamycin B or a pharmaceutically acceptable acid addition salt thereof, as the active ingredient, in association with a pharmaceutically acceptable solid or liquid carrier for the active ingredient.

The minimum inhibitory concentration (MIC, mcg/ml) of 3',4'-dideoxy-3'-fluorokanamycin B (abbreviated as 3',4'-dideoxy-3'-F-KMB) according to this invention against various bacteria were determined by a standard serial dilution method.

The antibacterial spectra of 3',4'-dideoxy-3'-fluorokanamycin B in the form of the free base are shown in Table 1 below. For comparison, the antibacterial spectra of kanamycin B and 3'-fluoro-3'-deoxykanamycin B (abbreviated as 3'-F-KMB) are also shown in the Table 1.

As will be clear from the antibacterial spectra of Table 1, 3',4'-dideoxy-3'-fluorokanamycin B of this invention exhibits an antibacterial activity higher than that of 3'-fluoro-3'-deoxykanamycin B even against various resistant bacteria which are capable of producing the phosphorylating enzyme or the adenylating enzyme acting on the 4'-hydroxyl group of 3'-fluoro-3'-deoxykanamycin B.

wherein Ts is tosyl group, which is disclosed in Japanese patent application first publication "Kokai" No. 63993/81 and U.S. Pat. No. 4,349,666. Then, we have found that when this Compound (a) is reacted with 1.5 to 5 molar proportions of N-acetylimidazole per mol of Compound (a) at a temperature of 0° to 50° C. in dry dimethylsulfoxide in the presence of pyridine, the 2"-hydroxy group of Compound (a) is preferentially acetylated without involving the acetylation of the 3'-hydroxyl group of Compound (a). We have also found that when the 6'-N,4'-O-carbonyl-4''',6"-O-cyclohexylidene-2"-O-acetyl-1,2',3,3"-tetra-N-tosylkanamycin B so formed [hereinafter referred to as Compound (b)] is reacted with a benzylsulfonylating agent such as benzylsulfonyl chloride, a mesylating agent such as mesyl

TABLE 1

| | M.I.C. (mcg/ml) | | |
|---|---|---|---|
| Test organisms | 3',4'-Dideoxy-3'-F-KMB(this invention) | 3'-F-KMB (Comparative) | Kanamycin B (Comparative) |
| Staphylococcus aureus 209P | 0.39 | 0.78 | 0.78 |
| Staphylococcus aureus Smith | 0.39 | 0.39 | 0.2 |
| Staphylococcus aureus Ap 01 | 0.78 | 50 | 50 |
| Staphylococcus epidermidis 109 | 1.56 | 50 | 100 |
| Micrococcus flavus FDA 16 | 1.56 | 3.12 | 3.12 |
| Corynebacterium bovis 1810 | 0.78 | 0.78 | 1.56 |
| Escherichia coli NIHJ | 0.39 | 0.39 | 0.39 |
| Escherichia coli K-12 | 0.39 | 0.78 | 0.39 |
| Escherichia coli ML1629 | 0.78 | 0.78 | <100 |
| Mycobacterium 607 | 0.39 | 0.78 | 1.56 |
| Klebsiella pneumoniae | 0.78 | 0.78 | 0.78 |
| Proteus rettgeri GN 311 | <0.2 | 0.39 | 0.78 |
| Pseudomonas aeruginosa A3 | <0.2 | <0.2 | 1.56 |
| Pseudomonas aeruginosa No 12 | 3.12 | 3.12 | 12.5 |
| Pseudomonas aeruginosa H-9 | 3.12 | 3.12 | <100 |
| Pseudomonas aeruginosa TI-13 | 3.12 | 3.12 | 25 |
| Pseudomonas aeruginosa 99 | 6.25 | 6.25 | 50 |

The preparation of 3',4'-dideoxy-3'-fluorokanamycin B according to this invention is now described. When we have now invented a process of producing 3',4'-dideoxy-3'-fluorokanamycin B, we have utilized our several findings which we obtained during our research on the synthesis of 3'-fluoro-3'-deoxykanamycin B from kanamycin B and have started from some new intermediates as prepared at that time.

When we made our researches to provide a method for the synthesis of the 3'-deoxy-3'-fluorokanamycin B starting from kanamycin B, we used, as an intermediate product, a known N,O-protected derivative of kanamycin B, namely 6'-N,4'-O-carbonyl-4''',6"-O-cyclohexylidene-1,2',3,3"-tetra-N-tosyl-kanamycin B [hereinafter referred to as Compound (a)] of the formula (a):

chloride or a tosylating agent such as tosyl chloride in dry pyridine at a temperature of up to 50° C., the 3'-hydroxyl group of Compound (b) can substantially selectively be sulfonylated, while the 5-hydroxyl group of Compound (b) is not or little sulfonylated, so that 3'-O-sulfonyl-6'-N,4'-O-carbonyl-4''',6"-O-cyclohexylidene-2"-O-acetyl-1,2',3,3"-tetra-N-tosyl-kanamycin B [hereinafter referred to as Compound (c)] is formed; that the benzylsulfonylating agent is most suitable for the selective sulfonylation of the 3'-hydroxyl group of Compound (b); and that when Compound (b) is sulfonylated with a mesylating agent, the 5-hydroxyl group of Compound (b) can also be partially sulfonylated to give such a 3',5-di-O-sulfonylated derivative of Compound (b) as a minor byproduct, which can then easily be separated by chromatographic method from the desired product, the mono-3'-O-sulfonylated derivative [the Compound (c)] of Compound (b). Further, we have found that when Compound (c) is treated with 2-10 molar proportions of an alkali metal hydroxide such as sodium hydroxide per mol of Compound (c) at a concentration of 1-5% (by weight) of the alkali metal hydroxide in dry methanol, dry ethanol or dry benzylalcohol at a temperature ranging from 0° C. to the boiling point of the alcohol used and for a reaction time of 5 minutes to 2 hours or longer, the 3'-sulfonyloxy group of Compound (c) can be reacted with the 2'-tosylamino group of the same molecule of Compound (c) to make the formation of the aziridine ring, and concurrently the cleavage of the 2''-O-acetyl group is involved, and also concurrently one end of the linkages of the carbonyl group (O=C<) bridging between the 6'-amino group and the 4'-hydroxyl group in the same molecule of Compound (c) is liberated from the 4'-hydroxyl group and is reacted with the co-existing methanol, ethanol or benzyl alcohol to have the 6'-amino group converted into the methoxycarbonylamino group, ethoxycarbonylamino group or benzyloxycarbonylamino group. Thus, there is consequentially yielded 4'',6''-O-cyclohexylidene-3'-deoxy-3'-epi-2',3'-(N-tosyl)epimino-6'-N-methoxy (or ethoxy or benzyloxy) carbonyl-1,3,3''-tri-N-tosylkanamycin B [hereinafter referred to as Compound (d)] of the formula:

wherein Ts is tosyl group; A' is methoxycarbonyl group, ethoxycarbonyl group or benzyloxycarbonyl group.

Furthermore, we have found that when Compound (d) obtained as above is reacted with sodium hydrogen difluoride or potassium hydrogen difluoride in a polar organic solvent (employed as the reaction medium), for example, in dry dimethylformamide or dry dimethylacetamide under heating, for example, at a temperature of 120° to 200° C. and for a reaction time of about 10 minutes to 20 hours, the 2',3'-aziridine ring of Compound (d) is fissioned and the fluoro group is introduced into the 3'-position, so that 4'',6''-O-cyclohexylidene-3'-deoxy-3'-fluoro-6'-N-methoxy (or ethoxy or benzyloxy) carbonyl-1,2',3,3''-tetra-N-tosylkanamycin B [hereinafter referred to as Compound (e)] is formed. As long as we are aware of, it is a first discovery of us in the field of chemistry of sugars, including aminoglycosidic antibiotics, to find out that a kanamycin B derivative can have been fluorinated at the 3'-position thereof when an alkali metal hydrogen difluoride is reacted therewith.

When Compound (e) as above is then subjected to the conventional deprotecting procedures for removal of the amino-protecting groups at the 6'-, 1-, 2'-, 3- and 3''-amino groups and also for removal of the hydroxyl-protecting group (cyclohexylidene group) at the 4''- and 6''-hydroxyl groups, 3'-fluoro-3'-deoxykanamycin B as desired is formed.

In our further researches, we have found that Compound (d) as above can be treated so as to remove therefrom the methoxycarbonyl, ethoxycarbonyl or benzyloxycarbonyl group from the 6'-amino group, and also to remove the hydroxyl-protecting cyclohexylidene group bridging between the 4''- and 6''-hydroxyl groups of Compound (d), affording 3'-deoxy-3'-epi-2',3'-(N-tosyl)epimino-1,3,3''-tri-N-tosylkanamycin B; that the free 6'-amino group of the resulting 3'-deoxy-3'-epi-2',3'-(N-tosyl)epimino-1,3,3''-tri-N-tosylkanamycin B may be protected again by introducing thereinto freshly such an amino-protecting group of a sort different from that of the previous amino-protecting group which was used for the preparation of Compound (d) as above, provided that such an amino-protecting group to be freshly introduced may be an alkanoyl group or an aroyl group but should not be of a sulfonyl type; that there is thus prepared an N-protected-3'-deoxy-3'-epi-2',3'-epimino-kanamycin B having a desirable 6'-amino-protecting group, and that when the resulting N-protected-3'-deoxy-3'-epi-2',3'-epiminokanamycin B so prepared can be reacted with an alkali metal hydrogen difluoride in a similar manner as above, desirable N-protected-3'-deoxy-3'-fluorokanamycin B compound is obtained.

Moreover, we have found the following: With the aforesaid Compound (a) which was used as the starting compound in the process for synthesis of 3'-deoxy-3'-fluorokanamycin B, the amino-protecting group for protecting the 1-, 2'-, 3- and 3''-amino groups was the tosyl group, and the hydroxyl-protecting group for blocking both the 4'' and 6''-hydroxyl group in combination was the cyclohexylidene group. Now, however, it has been found that such an otherwise N,O-protected derivative of kanamycin B which may be useful as an intermediate product equivalent to Compound (a) may be prepared by using, in place of said tosyl group, such a known amino-protecting group of the sulfonyl type which can serve equivalently to said tosyl group; and using in place of said cyclohexylidene group, such a known hydroxyl-protecting group which can serve equivalently to said 4'',6''-O-cyclohexylidene group, and that the otherwise N,O-protected kanamycin B derivative so prepared may be processed in a similar manner as above to afford such a 4'',6''-di-O-protected-1,3,3''-tri-N-sulfonylated (protected)-3'-deoxy-3'-epi-6'-N-methoxy (or ethoxy or benzyloxy) carbonyl-2',3'-(N-sulfonylated, protected) epimino-kanamycin B which may be a useful intermediate product equivalent to the aforesaid Compound (d).

Based on our many findings as just described above, we have discovered that broadly, an N,O-protected 3'-deoxy-3'-epi-2',3'-epimino-kanamycin B derivative of the general formula:

(f)

wherein A″ is an amino-protecting group of a sort which is not an amino-protecting group of the sulfonyl type, or A″ is a hydrogen atom; B is an amino-protecting group selected from an alkylsulfonyl group, an aralkylsulfonyl group and an arylsulfonyl group; Q is an alkylsulfonyl group, an aralkylsulfonyl group or an arylsulfonyl group; X and Y are each a hydrogen atom or a mono-valent hydroxyl-protecting group, or X and Y as taken together form a divalent hydroxyl-protecting group can be reacted with an alkali metal hydrogen difluoride of the formula:

MeHF$_2$ (g)

wherein Me is an alkali metal atom, in an organic solvent under heating, to produce such an N,O-protected 3′-deoxy-3′-fluoro-kanamycin B derivative of the general formula:

(h)

wherein A″, B, Q, X and Y are as defined above [referred to as Compound (h)], and that when any of the amino-protecting groups (A″ and B) and/or any of the hydroxyl-protecting groups (X and Y) are remaining in Compound (h), these remaining amino-protecting groups and hydroxyl-protecting groups may be removed along with the removal of the 2′-amino-blocking sulfonyl group (Q) by known deprotecting procedures to yield the 3′-deoxy-3′-fluorokanamycin B of the formula:

(i)

as described in the Japanese patent application No. 262700/84.

We, have now made a further research in an attempt to synthetize 3′,4′-dideoxy-3′-fluorokanamycin B with utilizing the N,O-protected 3′-deoxy-3′-fluorokanamycin B derivative of the above formula (h) which was obtained as an intermediate in the aforesaid synthetic method of producing 3′-deoxy-3′-fluorokanamycin B. As a result, we have found that when the above Compound (h) is reacted with 1.5 to 5 molar proportions of N-acetylimidazole, N-benzoylimidazole or benzoyl chloride per mol of Compound (h) in dry dimethylsulfoxide in the presence of pyridine at a temperature of 0° to 50° C., the 2″-hydroxyl group of Compound (h) can be preferentially protected by the acetylation or benzoylation without involving the acetylation or benzoylation of the 4′-hydroxyl group of Compound (h), and that when the 4″,6″-O-protected-2″-O-acetyl- or 4″,6″-O-protected-2″-O-benzoyl-1,2′,3,3″,6″-penta-N-protected-3′-deoxy-3′-fluorokanamycin B thus obtained [hereinafter referred to as compound (j)] is then reacted with a benzylsulfonylating agent such as benzylsulfonyl chloride or a mesylating agent such as mesyl chloride or a tosylating agent such as tosyl chloride, in an organic solvent containing dry pyridine at a temperature of up to 50° C., the 5-hydroxyl group of Compound (j) can not or little be sulfonylated, whereas the 4′-hydroxyl group of Compound (j) can be substantially selectively sulfonylated to afford a 4′-O-sulfonyl-4″,6″-O-protected-2″-O-acetyl- or 4′-O-sulfonyl-4″,6″-O-protected-2″-O-benzoyl-1,2′,3,3″,6″-penta-N-protected-3′-deoxy-3′-fluorokanamycin B [hereinafter referred to as Compound (k)].

We have also found that when the 4′-O-sulfonylated product (Compound (k)) so obtained is then reacted with a bromide or iodide of an alkali metal or another metal, the reaction of replacing the 4′-sulfonyloxy group by a bromine or iodine atom can substantially be completed in a reaction time of 30 minutes to about 2 hours, even if the concentration of the metal halide used as the halogenation reagent is in a range of 3 to 50% by weight, and that the 4′-sulfonyloxy group of the 4′-O-sulfonylated product (Compound (k)) can be replaced by a chloro group by reacting with a chloride of an alkali metal or another metal.

Furthermore, we have now found that when the 4′-halogenated 3′-deoxy-3′-fluorokanamycin B compound (hereinafter referred to as Compound (l)) as derived from Compound (k) by the above-mentioned procedures is further subjected to a reduction reaction, the 4′-halo group of Compound (l) can be removed therefrom without involving the removal of the 3′- fluoro group, with the consequence that the removal of the 4'-hydroxyl group of the kanamycin B molecule, that is to say, the 4'-deoxygenation of the 3'-deoxy-3'-fluoro kanamycin B takes place without invoking the cleavage of the 3'-fluoro group. That similar procedures for the sulfonylation of 3'-hydroxyl group of kanamycin B, the subsequent 3'-halogenation (the substitution for a halogen) of the 3'-sulfonyloxy group and removal of the 3'-halo group by reduction are applicable to the synthesis of 3'-deoxykanamycin B from kanamycin B is disclosed in the Japanese patent application first publication "Kokai" No. 63993/81.

The 4'-deoxy derivative [referred to as Compound (m)] which has thus been produced from the 4'-halogenated Compound (l) through the above-mentioned removal of the 4'-halo group by the reduction is still containing therein the remaining amino-protecting groups (A", B, Q) as well as the remaining 2"-, 4"- and 6"-O-protecting groups (the acetyl group or benzoyl group; as well as X and Y). Removal of these remaining protecting groups from Compound (m) by known deprotecting methods can give the desired compound, 3',4'-dideoxy-3'-fluorokanamycin B.

Thus, through our further researches now made, we have found out that the new compound, 3',4'-dideoxy-3'-fluorokanamycin B can be synthetized starting from the aforesaid particular Compound (a) or from such an N,O-protected kanamycin B derivative which is equivalent to the Compound (a) and which is obtainable by replacing the amino-protecting groups (mainly, the tosyl groups) of Compound (a) by another amino-protecting groups and replacing the hydroxyl-protecting groups (the 4",6"-O-cyclohexylidene group) of Compound (a) by another hydroxyl-protecting groups, when there is employed a synthetic route where a series of the reaction stages of preparing successively the intermediate Compounds (b), (c), (d), (e), (f), (h), (j), (k) and (l) is effected, or even when a similar synthetic route is resorted on.

According to a third aspect of this invention, therefore, there is provided a process for preparing 3',4'-dideoxy-3'-fluorokanamycin B of the formula:

which comprises the steps of:

(i) reacting a 3'-deoxy-3'-fluoro-4'-O-sulfonylkanamycin B derivative of the general formula:

wherein R is an alkyl group, an aralkyl group or an aryl group; A is an amino-protecting group selected from methoxycarbonyl group, ethoxycarbonyl group and benzyloxycarbonyl group, or A is an amino-protecting group selected from an alkanoyl group, an aroyl group and a sulfonyl group; B is an amino-protecting group selected from an alkylsulfonyl group, an aralkylsulfonyl group and an arylsulfonyl group; X and Y are each a hydrogen atom or a mono-valent hydroxyl-protecting group, or X and Y as taken together form a di-valent hydroxyl-protecting group; Q is an alkylsulfonyl group, an aralkylsulfonyl group or an arylsulfonyl group same as the group B; and V is a hydroxyl-protecting group, with a metal halide of the formula:

$$MD \qquad (III)$$

wherein M is a metal atom and D is a chlorine, bromine or iodine atom, to produce a 4'-halogenated product of the formula:

wherein A, B, Q, V, X, Y and D are as defined above, (ii) reducing the 4'-halogenated product of the formula (IV) so obtained in the step (i) to replace the 4'-halo group by a hydrogen atom and to form a corresponding N,O-protected 3',4'-dideoxy-3'-fluorokanamycin B derivative, and (iii) removing the remaining amino-protecting groups (A, B, Q) and the remaining hydroxyl-protecting groups (V, X, Y) from the resultant N,O-protected 3',4'-dideoxy-3'-fluorokanamycin B derivative by known deprotecting methods.

In the process according to the third aspect of this invention, the 6'-amino-protecting group (A) present in the N,O-protected 3'-deoxy-3'-fluoro-4'-O-sulfonylkanamycin B derivative of the formula (II) is any of the known amino-protecting groups which do not participate in the concerned reactions and which include, for example, an acyl group, particularly an alkanoyl group such as acetyl group and trifluoroacetyl group; an aroyl group such as benzoyl group; an alkoxycarbonyl group such as methoxycarbonyl group, ethoxycarbonyl group and butoxycarbonyl group; an aralkyloxycarbonyl group such as benzyloxycarbonyl group and phenethyloxycarbonyl group; an aryloxycarbonyl group such as phenoxycarbonyl group and methoxyphenoxycarbonyl group; as well as an amino-protecting group of sulfonyl type, for example, an alkylsulfonyl group such as mesyl group and trifluoromethylsulfonyl group, an aralkylsulfonyl group such as benzylsulfonyl group, and an arylsulfonyl group such as tosyl group. The symbol (A) in the compound (II) formula can denote even a hydrogen atom. However, it is preferred that the 6'-amino group of the compound (II) has been protected.

The 1-, 3-, and 3''-amino groups of the compound of the formula (II) have been protected with a suitable amino-protecting group (B) which is selected from an alkylsulfonyl group such as mesyl group and trifluoromethylsulfonyl group, an aralkylsulfonyl group such as benzylsulfonyl group, and an arylsulfonyl group such as tosyl group.

The sulfonyl group (Q) which is bonding to the 2'-amino group of the compound (II) may be the same as or different from the amino-protecting sulfonyl group (B) defined above, depending on the kind of the sulfonylating agent which was used in the process of preparing the compound (II). However, it is usually preferred that the group (Q) should be of the same kind as the sulfonyl group of protecting the group (B).

The hydroxyl-protecting groups (X) and (Y) which protect the 4''-hydroxyl-group and the 6''-hydroxyl group of the compound (II) each may be an ordinary known mono-valent hydroxyl-protecting group. Examples of the mono-valent hydroxyl-protecting group for this purpose include a lower alkyl group, an aryl group such as phenyl group, an alkanoyl group such as acetyl group and an aroyl group such as benzoyl group. Alternatively, the groups (X) and (Y) as taken together may form a known di-valent hydroxyl-protecting group. Examples of the di-valent hydroxyl-protecting groups for this purpose include a lower alkylidene group such as isopropylidene group, an aralkylidene group such as benzylidene group, a cycloalkylidene group such as cyclohexylidene group, and a tetrahydropyranylidene group. Introduction of the above-mentioned amino-protecting groups and the 4''- and 6''-hydroxyl-protecting group(s) into the molecule of kanamycin B may be performed by such procedures as disclosed, for example, in Japanese patent application first publication "Kokai" No. 105699/80, U.K. Pat. No. 2,043,634 B, U.S. Pat. No. 4,357,466, Japanese patent application first publication "Kokai" No. 152497/81 and U.S. Pat. No. 4,359,572.

The 2''-hydroxyl-protecting group (V) of the compound (II) is a lower alkanoyl group such as acetyl group or an aroyl group such as benzoyl group. The 2''-hydroxyl-protecting group (V) can be introduced into the 2''-hydroxyl group by reacting it e.g. with an N-alkanoylimidazole such as N-acetylimidazole or N-benzoylimidazole, or with benzoyl chloride in dry dimethylsulfoxide in the presence of pyridine (see, for example, Example 1, step (D) of preparing Compound (e-1) given hereinafter).

In the process according to the third aspect of this invention, the compound of the formula (II) is reacted with a metal halide (MD) of the formula (III). The halogen (D) in the compound of the formula (II) may preferably be chlorine, bromine, or iodine atom but should not be fluorine atom. The metal (M) may be an alkali metal, an alkaline earth metal or even a heavy metal. In practice, however, it is preferable to use lithium chloride, lithium bromide, lithium iodide or sodium iodide as the metal halide (III). The metal halide (III) may preferably be employed in such a proportion of a few moles to 100 moles per mole of the compound of the formula (II). The solvent to be used for the reaction medium may preferably be an organic solvent in which both of the starting compound (II) and the reactant (III) are soluble. Examples of the solvent include dimethylformamide, hexamethylphosphoric triamide and dimethylsulfoxide, or the solvent may also be a mixtures of such solvent of a sort just mentioned above with an ordinary aprotic solvent of a neutral nature.

The 4'-halogen-substitution reaction of reacting the compound (II) with the metal halide (III) may conveniently be conducted at a temperature of 0° to 150° C. and for a reaction time of 30 minutes to about 2 hours. For the removal of the 4'-halo group from the 4'-halogenated product (IV) thus obtained, the compound (IV) is reduced by treatment with the butyltin hydride for the reductive replacement of the 4'-halo group with a hydrogen atom, or by a catalytic hydrogenation in the presence of Raney nickel as catalyst, in a known manner, to produce, an N,O-protected 3',4'-dideoxy-3'-fluorokanamycin B derivative.

The N,O-protected 3',4'-dideoxy-3'-fluorokanamycin B derivative so prepared may be recovered from the reaction solution by extracting the reaction solution with a suitable organic solvent such as ethyl acetate, followed by isolation and purification by silica gel column chromatography.

The subsequent removal of the remaining amino-protecting groups (A, B, Q) and/or the remaining hydroxyl-protecting groups (V, X, Y) may be achieved by conventional deprotecting techniques as properly chosen depending on the kinds of the N,O-protecting groups to be removed and may be effected in two or more separate stages. For example, the above-mentioned N,O-protected 3',4'-dideoxy-3'-fluorokanamycin B derivative may be treated at first with a metal in liquid ammonia according to a known method disclosed in Japanese patent application first publication "Kokai" No. 71446/78 or U.K. Pat. No. 1,555,661, so that the amino-protecting sulfonyl groups (B, Q and occasionally also A) are removed. The resulting partially deprotected product now freed from the sulfonyl groups (B, Q) may then be subjected to hydrolysis with acid and hydrogenolysis to remove the 6'-N-protecting group (A) and the 4'',6''-O-protecting group (X and Y; such as an alkylidene group, a cycloalkylidene group or an aralkylidene group) as well as the 2''-O-protecting group (V; such as the acyl group), so that the desired compound, 3',4'-dideoxy-3'-fluorokanamycin B of the formula (I) is finally produced.

The reaction solution as obtained from the final stage for the deprotection reactions as above is concentrated and the solid residue is dissolved in water. The resulting aqueous solution is purified by column chromatography on CM-Sephadex C-25 as developed by aqueous ammonia as eluent, to afford the desired compound, 3',4'-dideoxy-3'-fluorokanamycin B [Compound (I)].

Furthermore, according to a fourth aspect of this invention, there is provided a process for producing 3′,4′-dideoxy-3′-fluorokanamycin B of the formula:

which comprises the steps of:

(i) reacting an N,O-protected 3′-O-sulfonyl-6′-N,4′-O-carbonyl-kanamycin B derivative of the general formula:

wherein B is an amino-protecting group selected from an alkylsulfonyl group, an aralkylsulfonyl group and an arylsulfonyl group; X and Y are each a hydrogen atom or a mono-valent hydroxyl-protecting group, or X and Y as taken together form a di-valent hydroxyl-protecting group; Q is an alkylsulfonyl group, an aralkylsulfonyl group or an arylsulfonyl group same as the group B; Z is an alkylsulfonyl group, an aralkylsulfonyl group or an arylsulfonyl group which is the same as or different from the group Q, and V′ is a hydroxyl-protecting group or a hydrogen atom, with an alkali metal hydroxide in the presence of methanol, ethanol or benzyl alcohol, to produce an N,O-protected 3′-deoxy-3′-epi-2′,3′-epimino-6′-N-alkoxy- or aralkyloxy-carbonylkanamycin B derivative of the general formula:

wherein B, X, Y, Q and V′ are as defined above; A′ is an amino-protecting group selected from methoxycarbonyl group, ethoxycarbonyl group and benzyloxycarbonyl group, (ii) reacting the resulting compound of the formula (VI) with an alkali metal hydrogen difluoride of the formula:

$$MeHF_2 \quad (VII)$$

wherein Me is an alkali metal atom, in an organic solvent under heating, to produce a 3′-deoxy-3′-fluorokanamycin B derivative of the general formula:

wherein A′ is the amino-protecting group selected from methoxycarbonyl group, ethoxycarbonyl group and benzyloxycarbonyl group; B is an amino-protecting group as defined above; V′, X and Y are as defined above, (iii) protecting the 2″-hydroxyl group of the compound of the formula (VIII) with a hydroxyl-protecting group optionally, when the compound (VIII) is containing the hydrogen atom for the symbol V′,

(iv) reacting the compound of the formula (VIII) where V′ is a hydroxyl-protecting group, with a sulfonic acid halide of the formula:

$$RSO_2D' \quad (IX)$$

wherein R is an alkyl group, an aralkyl group or an aryl group and D′ is a chlorine, bromine or iodine atom, or with a corresponding sulfonic anhydride of the formula:

$$(RSO_2)_2O \quad (IX')$$

wherein R is as defined above, to produce a 3'-deoxy-3'-fluoro-4'-O-sulfonylkanamycin B derivative of the formula:

(II')

wherein R is an alkyl group, an aralkyl group or an aryl group; A' is an amino-protecting group selected from methoxycarbonyl group, ethoxycarbonyl group and benzyloxycarbonyl group; B is an amino-protecting group selected from an alkylsulfonyl group, an aralkylsulfonyl group and an arylsulfonyl group; X and Y are each a hydrogen atom or a mono-valent hydroxyl-protecting group, or X and Y as taken together form a di-valent hydroxyl-protecting group; Q is an alkylsulfonyl group, an aralkylsulfonyl group or an arylsulfonyl group which is the same as the group B; V is a hydroxyl-protecting group, (v) reacting the compound of the formula (II) with a metal halide of the formula:

MD       (III)

wherein M is a metal and D is a chlorine, bromine or iodine atom, to produce a 4'-halogenated product of the formula:

(IV')

wherein A', B, Q, V, X, Y and D are as defined above, (vi) reducing the compound of the formula (IV') to substitute a hydrogen atom for the 4'-halo group (D) of the compound (IV') and thereby to produce a corresponding N,O-protected 3',4'-dideoxy-3'-fluorokanamycin B derivative, and (vii) removing the remaining amino-protecting groups (A', B, Q), as well as the remaining hydroxyl-protecting groups (V, X, Y) from the resultant N,O-protected 3',4'-dideoxy-3'-fluorokanamycin B derivative by known deprotecting methods.

The amino-protecting group (B) and the hydroxyl-protecting groups (V, X, Y) present in the protected 3'-O-sulfonyl-6'-N,4'-O-carbonyl-kanamycin B derivatives of the general formula (V) which is used as the starting compound in the process of the fourth aspect of this invention may respectively be the same as the amino-protecting group (B) and the hydroxyl-protecting groups (V, X, Y) which are present in the protected 3'-deoxy-3'-fluoro-4'-O-sulfonylkanamycin B derivatives of the general formula (II) used as the starting compound in the process of the third aspect of this invention. However, the symbol (V') of the compound formula (V) may also show a hydrogen atom, that is to say, such compound (V) where the 2"-hydroxyl group remains unprotected may be also employed, if desired. The 3'-O-sulfonyl group (Z) of the compound (V) may be an alkylsulfonyl group containing 1 to 4 carbon atoms, such as methanesulfonyl (or mesyl) group and ethanesulfonyl group; an aralkyl group such as benzylsulfonyl group; and an arylsulfonyl group such as tosyl group. Benzylsulfonyl group is preferred for the group Z.

The reaction of the 3'-O-sulfonyl-kanamycin B derivative of the formula (V) with an alkali metal hydroxide such as sodium hydroxide is conducted in the presence of methanol, ethanol or benzyl alcohol under anhydrous conditions. The alkali metal hydroxide may be added in 2 to 10 molar proportions per mol of the 3'-O-sulfonyl-kanamycin B derivative (V) and at such a concentration of the alkali metal hydroxide of 1 to 5% by weight in the reaction medium.

The reaction temperature may be in a range of 0° C. to the refluxing temperature of the reaction medium (the solvent used). The reaction may be completed in a reaction time of 5 minutes or more. Even if the reaction time is prolonged, any undesirable by-product is not produced so much. In this case, however, it is preferable that the reaction of the compound (V) with an alkali metal hydroxide should be effected under such reaction conditions that do not liberate the methoxycarbonyl, ethoxycarbonyl or benzyloxycarbonyl group (A') from the 6'-amino-group of the 2',3'-epimino compound of the formula (VI) as produced.

In the process according to the fourth aspect of this invention, the 2',3'-epimino compound of the formula (VI) so produced as an intermediate is then reacted with an alkali metal hydrogen difluoride of the formula (VII), and this reaction stage may be carried out as follows. Thus, the alkali metal hydrogen difluoride (VII) to be used in this reaction stage may be NaHF$_2$, KHF$_2$ or LiHF$_2$, but KHF$_2$ is most preferred for this purpose. The reaction may be conducted in a suitable dry organic solvent, and preferably in a polar organic solvent such as dimethylformamide, dimethylacetamide, acetonitrile or sulfolane. Dimethylformamide is most suitable. It is necessary to select an appropriate organic solvent which can allow the desired reaction to proceed smoothly. The reaction my be performed at a temperature ranging from 120° to 200° C., preferably from 150° to 160° C. under heating.

The N,O-protected 3'-deoxy-3'-fluorokanamycin B derivative of the formula (VIII) so formed in the above reaction can be recovered by extracting the reaction solution with a suitable organic solvent such as ethyl acetate, followed by isolation and purification by silica gel column chromatography.

Where the compound of the formula (VIII) so produced is containing the 2"-hydroxyl group unprotected (namely, when the symbol (V') is the hydrogen atom), this compound (VIII) may be reacted with 1.5 to 5 molar proportions of N-acetylimidazole, N-benzoylimidazole or benzoyl chloride at a temperature of 0° to 50° C. in dry dimethylsulfoxide in the presence of pyridine. In this reaction, the 2″-hydroxyl group of the compound (VIII) can selectively be acetylated or benzoylated without involving the acetylation or benzoylation of the 4′-hydroxyl group, so that the 2″-hydroxyl-group can be protected with a hydroxyl-protecting acetyl or benzoyl group (V′).

Subsequently, the N,O-protected 3′-deoxy-3′-fluoro-kanamycin B derivative (VIII) so formed is reacted with a sulfonylating agent of the formula (IX) or (IX′) in the next step. To this end, the compound of the formula (VIII) may be dissolved in a suitable organic solvent such as pyridine and reacted with the sulfonic acid halide $RSO_2D'$ of the formula (IX), preferably an arylsulfonic acid halide or with a corresponding sulfonic anhydride of the formula (IX′), preferably an arylsulfonic anhydride, to effect the selective sulfonylation of the 4′-hydroxyl group of the compound (VIII) and thereby to give the compound of the formula (II′). For this selective 4′-O-sulfonylation, pyridine may most conveniently be used as the reaction medium. However, any of the aprotic organic solvent which are capable of dissolving perfectly or partially the compound (VIII) may be used as the reaction medium for the selective 4′-O-sulfonylation. Examples of the organic solvent for this purpose are dimethylformamide, dimethylacetamide, dimethylsulfoxide, tetrahydrofuran, dioxane, diethyl ether, chloroform, benzene, sulfolane and the like. Usually, the selective 4′-O-sulfonylation of the compound (VIII) may be effected in said organic solvent in the presence of an organic basic substance such as picoline, N-acetylmorpholine or triethylamine dissolved in said solvent.

The sulfonic acid halide (IX) or the corresponding sulfonic anhydride (IX′) may preferably be used in an amount of from 1 to 5 moles per mole of the kanamycin B compound (VIII).

The preferred examples of the sulfonylating agent (IX) or (IX′) include tosyl chloride, toluensulfonic anhydride, benzylsulfonyl chloride and methanesulfonyl chloride. The temperature for the 4′-O-sulfonylation of the compound (VIII) may be in a range of −40° to 100° C., but preferably at −20° C. to 25° C., and the reaction time may suitably be in a range of 30 minutes to 2 days.

In the process according to the fourth aspect of this invention, the 4′-O-sulfonylated product of the formula (II′) is thus prepared as an intermediate product through the above-mentioned reaction steps. The following step of reacting the 4′-O-sulfonylated product (II′) with a metal halide (III), and the step of removing the 4′-halo group of the compound (IV′) by reduction, as well as the final deprotecting step may all be conducted in the same manner as in the corresponding steps of the process of the third aspect of this invention.

The pharmaceutical composition according to the aforesaid second aspect of this invention may be formulated into suitable forms for oral, parenteral or intrarectal administration. Composition in the form of injectable solution may contain 0.1% to 20.0% by weight of the compound (I) as active ingredient, and also one or more of a pH-adjuster, buffer, stabilizer, excipient, local anesthetics and an additive for rendering the solution isotonic. The injectable solution may be prepared to be adapted for subcutaneous, intramuscular or intravenous injection by any conventional pharmaceutical technique. Solid composition for oral administration which may be in the form of tablets, coated tablets, granules, powder and capsules, may contain excipients for the active ingredient, and if required, other additives, including disintegrators, lubricants, colorants, flavors and the like. The proportion of the active compound to the carrier may be at a ratio of 1:1 to 1:100 by weight and may usually be chosen appropriately depending on the form of the orally administrable formulation prepared. Suppository formulations may contain excipients and, if necessary, surfactant and lubricants additionally to the active compound.

The optimum dosage of the new compound (I) administered will, of course, depend on the mode of administration and the treatment aimed. For men, the unit dosage for injections generally contains from 50 mg to 200 mg of the compound (I), which may be administered intravenously or intramuscularly in divided doses one or more times per day. The new compound of the formula (I) used in the composition of this invention may be administered orally or an adult person at a dosage of 50 mg to 200 mg once a day.

This invention is now illustrated with reference to the following Examples. In the following Examples, Ac denotes acetyl group, Bz benzoyl group, Cbm methoxycarbonyl group, Z benzyloxycarbonyl group, Ts tosyl group, Bes benzylsulfonyl group, Tfl trifluoromethanesulfonyl group, and Ms mesyl group, unless otherwise stated.

EXAMPLE 1

(A) Preparation of 2″-O-acetyl-4′-O,6′-N-carbonyl-4″,6″-O-cyclohexylidene-1,3,2′,3″-tetra-N-tosylkanamycin B [Compound (b) mentioned hereinbefore]

Compound (b)

6′-N,4′-O-Carbonyl-4″,6″-O-cyclohexylidene-1,2′,3,3″-tetra-N-tosylkanamycin B [Compound (a) mentioned hereinbefore] (1.58 g) was dissolved in a mixture (7.9 ml) of dry dimethylsulfoxide and dry pyridine (9:1), to which was added N-acetylimidazole (0.58 g). The resulting mixture was allowed to stand at room temperature for 24 hours to effect the acetylation of the 2″-hydroxyl group of the starting compound, 6′-N,4′-O-carbonyl-4″,6″-O-cyclohexylidene-1,2′,3,3″-tetra-N-tosylkanamycin B [Compound (a)]. The reaction solution was poured into a saturated aqueous sodium hydrogen carbonate solution (160 ml). A solid as precipitated was recovered by filtration, washed with water and dried, affording 1.6 g of the titled Compound (b).

(B) Preparation of 2″-O-acetyl-3′-O-benzylsulfonyl-4′-O-6′-N-carbonyl-4″,6″-O-cyclohexylidene-1,3,2′,3″-tetra-N-tosylkanamycin B [Compound (c-1)]

Compound (c-1)

Compound (b) (115 mg) obtained in the step (A) above was dissolved in dry pyridine (2 ml), to which was added benzylsulfonyl chloride (27 mg). The resulting mixture was stirred at −20° C. for 5 hours, to effect the 3′-O-benzylsulfonylation.

A small volume of water (0.02 ml) was added to the reaction solution, and the solution was concentrated. The residual solid was washed with a large volume of water and dried, to afford the titled Compound (c-1) as a colorless solid (125 mg).

(C) Preparation of 4″,6″-O-cyclohexylidene-3′-deoxy-3′-epi-6′-N-methoxycarbonyl-1,3,3″-tri-N-tosyl-2′,3′-(N-tosyl-)epiminokanamycin B [Compound (d-1)]

Compound (d-1)

Compound (c-1) (140 mg) obtained in the step (C) above was dissolved in dry methanol (3.2 ml) containing 0.5M sodium hydroxide. The resulting mixture was stirred at room temperature for 3 hours to effect the reaction. The reaction solution was neutralized by the addition of 1M aqueous hydrochloric acid to a neutral pH and then concentrated to dryness. The residual solid was washed with a large volume of water and dried, to afford the titled Compound (d-1) as a colorless solid (117 mg).

(D) Preparation of 4″,6″-O-cyclohexylidene-3′-deoxy-3′-fluoro-6′-N-methoxycarbonyl-1,3,2′,3″-tetra-N-tosylkanamycin B [Compound (e-1)]

Compound (e-1)

Compound (d-1) (116.4 mg) obtained in the step (C) above was dissolved in dimethylformamide (2.3 ml), to which was added potassium hydrogen fluoride (KHF$_2$) (37 mg). The resulting mixture was stirred at 150° C. for 2 hours. The reaction solution was cooled and poured into a saturated aqueous sodium hydrogen carbonate solution (47 ml). A solid as precipitated was recovered by filtration and then washed with water. The solid thus obtained was dissolved in chloroform, and the resultant solution was subjected to silica gel column chromatography [Wakogel C-200 (6 g), as developed with chloroform-methanol (30:1)]. The fractions of the eluate containing the Compound (e-1) were combined together and concentrated. Thus, a crude solid product (75.7 mg) mainly comprising Compound (e-1) was obtained in the form of a pale yellow solid. Chromatographic separation of this crude product into individual components did not get a success but $^{19}$F-NMR spectrum (in deutero-pyridine, CFCl$_3$ as internal standard) of this crude compound exhibited a clear double triplet at 193.4 ppm ($J_{F,H-3}$,55Hz, $J_{F,H-2}=J_{F,H-4}=12$Hz) which is attributable to the 3′-F of Compound (e-1).

(E) Preparation of 2″-O-acetyl-4″,6″-O-cyclohexylidene-3′-deoxy-3′-fluoro-6′-N-methoxycarbonyl-1,3,2′,3″-tetra-N-tosylkanamycin B [Compound (j-1)]

Compound (e-1) (244 mg, 0.197 m mole) obtained as the crude product in the step (D) above was dissolved in a mixture (1.22 ml) of dry dimethylsulfoxide (DMSO) and pyridine (9:1), to which was added N-acetylimidazole (86.6 mg, 0.786 m mole). The mixture so obtained was stirred at room temperature for 72 hours (for the 2″-O-acetylation). To the reaction solution, water (0.07 ml) was added to stop the reaction. The reaction solution was then added to a saturated aqueous sodium hydrogen carbonate solution (120 ml). A colorless solid precipitate as formed was recovered by filtration, washed with water and dried in vacuo. The solid thus dried was further washed with ethyl ether and dried again in vacuo to yield the title compound (j-1) as a pale yellow solid (250.3 mg). Yield 99%.

$^1$H-NMR (in pyridine d$_5$): 5.20 (dt, 1H, $J_{H-3',F}=52$, $J_{3',4'}=J_{3',2'}=9.2$ Hz, H-3′).

(F) preparation of 2″-O-acetyl-4″,6″-O-cyclohexylidene-3′-deoxy-3′-fluoro-6′-N-methoxycarbonyl-1,3,2′,3″-tetra-N-tosyl-4′-O-trifluoromethylsulfonylkanamycin B [Compound (k-1)]

Compound (k-1)

Compound (j-1) (250.3 mg, 0.195 m mole) obtained in the step (E) above was dissolved in dry dichloromethane (5 ml), to which was added dry pyridine (0.12 ml). The resulting mixture was then admixed with trifluoromethanesulfonic anhydride (0.13 ml; 4 molar proportions per mole of Compound (j-1)) at −20° C. under stirring. After stirring for 2.5 hours, water (0.07 ml) was added to the reaction solution to stop the reaction (the 4′-O-trifluoromethanesulfonylation). The reaction solution was then admixed with chloroform (20 ml), and the admixture was obtained was washed successively with saturated aqueous sodium hydrogen carbonate solution, with 5% aqueous potassium bisulfate solution and with water. The admixture so washed was then dried over anhydrous sodium sulfate and concentrated to dryness, to afford the titled Compound (k-1) as an unstable solid (288.8 mg).

(G) Preparation of 2″-O-acetyl-4″,6″-O-cyclohexylidene-3′,4′-dideoxy-4′-epi-chloro-3′-fluoro-6′-N-methoxycarbonyl-1,3,2′,3″-tetra-N-tosylkanamycin B [Compound (l-1)]

Compound (l-1)

Compound (k-1) (288.8 mg) obtained in the step (F) above was dissolved in dry dimethylformamide (DMF) (5.8 ml). The resulting solution was admixed with lithium chloride (86.5 mg; 10 molar proportions per mol of Compound (k-1)), and the mixture was stirred at 50° C. for 5 minutes (for the 4′-chlorination). The reaction mixture was then poured into water (116 ml). A pale yellow solid as precipitated was recovered by filtration, washed with water and dried under reduced pressure to afford a crude product comprising the titled Compound (l-1) as a solid (252 mg). This crude solid product was used as such in the next step without purification.

(H) Preparation of 2″-O-acetyl-4″,6″-O-cyclohexylidene-3′,4′-dideoxy-3′-fluoro-6′-N-methoxycarbonyl-1,3,2′,3″-tetra-N-tosylkanamycin B [Compound (m-1)]

Compound (m-1)

A crude product of Compound (l-1) (72.4 mg) obtained in the step (G) above was dissolved in dioxane (1.45 ml), to which were added α,α′-azobis-isobutyronitril (4.5 mg; 0.5 molar proportions per mole of Compound (l-1)) and tributyltin hydride (81 mg; 5 molar proportions per mole of Compound (l-1)). The resulting mixture was stirred at 80° C. under nitrogen atmosphere. After 5 minutes, α,α′-azobis-isobutylonitrile (4.5 mg) and tributyltin hydride (81 mg) were further added to the reaction mixture to complete the reduction reaction (for the reductive replacement of the 4′-chloro group by a hydrogen atom). After stirring for further 40 minutes, the reaction solution was concentrated under reduced pressure. The residue thus obtained was placed on the top of a column of silica gel ("Wakogel" C-200) (3.6 g). The column was washed with chloroform (110 ml) and eluted with a mixture of chloroform-acetone (2:1). The fractions of the eluate containing the desired compound were combined together and concentrated under reduced pressure to afford a crude product comprising the titled compound (59.8 mg). This crude product was dissolved in a mixture of chloroform and acetone (2:1) and was purified by silica gel column chromatography [Wako gel C-200 (3 g), eluent: chloroform-acetone (2:1)].

Amont the fractions of the eluate, the fractions as eluted from the total 3.5 ml volume to the total 9 ml volume of the eluate were combined together and concentrated to dryness under reduced pressure, to afford the titled Compound (m-1) (48.5 mg) as a colorless solid. Yield was 66% based on Compound (k-1).

$^1$H-NMR (in pyridine-d$_5$): δ3.61 (s, 3H, CH$_3$O.CO), 5.15 (m, 1H, H-3′).

(I) Production of 3′,4′-dideoxy-3′-fluorokanamycin B [Compound (I)]

Compound (m-1) obtained in the step (H), namely, the N,O-protected 3′-fluoro-3′,4′-dideoxykanamycin B was subjected to a series of the deprotecting stages for removal of the amino-protecting and hydroxyl-protecting groups as described below. Thus, Compound (m-1) (48.5 mg) was dissolved in dry tetrahydrofuran (THF). The resulting solution was added, under stirring, to a volume of liquid ammonia (about 15 ml) containing metallic sodium (about 80 mg) dissolved therein which had been cooled to −50° C. The mixture thus obtained was stirred at −50° C. for 10 minutes to effect removal of the tosyl groups from Compound (m-1). The reaction mixture was admixed with methanol to consume up the radical of the sodium metal. The resultant mixture was brought to room temperature to evaporate the ammonia therefrom. The residual syrup was concentrated to dryness to afford a colorless solid mainly comprising 2''-O-acetyl-4'',6''-O-cyclohexylidene-3',4'-dideoxy-3'-fluoro-6'-N-methoxycarbonylkanamycin B.

This colorless solid was dissolved in water (3.5 ml), and the resulting aqueous solution showed a strong alkalinity due to the sodium hydroxide remaining in said solid. Said aqueous solution was then heated to 80° C. and stirred at the same temperature for 2 hours to effect the hydrolysis and thereby to remove the methoxycarbonyl group (Cbm) and acetyl group (Ac) from the 2''-O-acetyl-4'',6''-O-cyclohexylidene-3',4'-dideoxy-3'-fluoro-6'-N-methoxycarbonylkanamycin B. The reaction solution containing 4'',6''-P-cyclohexylidene-3',4'-dideoxy-3'-fluorokanamycin B so formed as a partially deprotected product was cooled to room temperature, and admixed with an acidic cation-exchange resin; Dowex 50W×2 (H+ form, 200–400 mesh) (6 ml) to adsorb said partially deprotected product by the resin. By this treatment, the reaction solution was deprived of the sodium ion present in said reaction solution, and simultaneously additional hydrolysis of the partially deprotected product took place to remove the cyclohexylidene group from said partially deprotected product, and to produce the desired 3',4'-dideoxy-3'-fluorokanamycin B.

The cation-exchange resin (Dowex 50W×2) having adsorbed the desired 3',4'-dideoxy-3'-fluorokanamycin B therein was placed as such on the top of a further column of Dowex 50W×2 (H+ form) (200–400 mesh) (2 ml). The resin column was washed with water (40 ml) and eluted with 1M aqueous ammonia. The fractions of the eluate positive to the ninhydrin color reaction were collected and concentrated to dryness to yield a crude solid product. This crude product (23.2 mg) was dissolved in water (10 ml) and was subjected to Sephadex column chromatography. Thus, the aqueous solution (10 ml) of said crude solid product was passed into a column of CM-Sephadex C-25 (NH4+ form) (10 ml), which was then washed with water (50 ml). The Sephadex column was then eluted gradiently with aqueous ammonia with changing the concentration of the ammonia from 0.05M to 0.15M. The fractions of the eluate positive to the ninhydrin color reaction were collected together and concentrated to dryness, to give 3',4'-dideoxy-3'-fluorokanamycin B of the formula (I) (as the mono-carbonate) as a pale yellow solid (10.4 mg). Yield was 51%.

Figure 1:
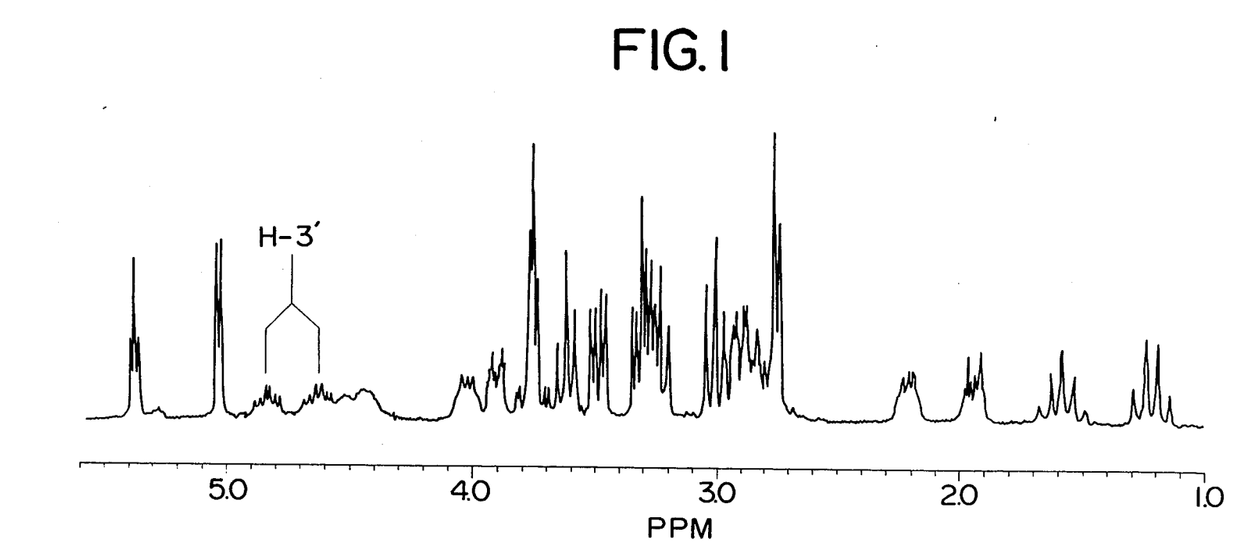

Specific rotation: $[\alpha]_D^{24} + 123°$ (c 1, water).

$^1$H-NMR (in $D_2O$ containing 20% $ND_3$): δ1.58 (quintet, 1H, H-4'$_{ax}$), 2.21 (m, 1H, H-4'$_{eq}$). 4.73 (ddt, 1H, H-3'), 5.37 (t, 1H, H-1'); $J_{H-1',F}=4$, $J_{H-3',F}=51.5$ Hz.

A chart of $^1$H-NMR spectrum of this compound of the formula (I) is shown in FIG. 1 of the accompanying drawing.

EXAMPLE 2

(A) Preparation of 4'',6''-O-isopropylidene-6'-N-benzyloxycarbonyl-1,3,2',3''-tetra-N-benzylsulfonyl-3'-deoxy-3'-fluorokanamycin B [Compound (e-2)]

3'-O-Benzylsulfonyl-4'-O,6'-N-carbonyl-4'',6''-O-isopropylidene-1,3,2',3''-tetra-N-benzylsulfonylkanamycin B [termed as Compound (c-2)] was treated with sodium hydroxide in anhydrous benzyl alcohol to afford 6'-N-benzyloxycarbonyl-1,3,3''-tri-N-benzylsulfonyl-2',3'-(N-benzylsulfonyl)epimino-3'-deoxy-3'-epi-4'',6''-O-isopropylidenekanamycin B [hereinafter referred to as Compound (d-2)] of the formula:

Compound (d-2)

Compound (d-2) (80 mg) thus obtained was dissolved in dimethylformamide (1.5 ml), to which was added potassium hydrogen fluoride (KHF2) (25 mg). The mixture was stirred at 150° C. for 2 hours. The reaction solution was processed in a similar manner to the step (D) of the Example 1 above, to afford a crude solid product (44 mg) comprising the titled Compound (e-2).

(B) Preparation of 2''-O-benzoyl-6'-N-benzyloxycarbonyl-1,3,2',3''-tetra-N-benzylsulfonyl-3'-deoxy-3'-fluoro-4'',6''-O-isopropylidenekanamycin B [Compound (j-2)]

Compound (j-2)

Compound (e-2) (600 mg) obtained in the step (A) above was dissolved in dry pyridine (1.5 ml), to which was added benzoyl chloride (14.3 mg). The mixture was allowed to stand at room temperature overnight (for the 2''-O-benzoylation). The reaction solution was admixed with water (0.02 ml) and the aqueous solution was poured into a saturated aqueous sodium hydrogen carbonate solution (50 ml). A solid precipitate as formed was recovered by filtration and dried. The solid obtained was purified by silica gel column chromatography (developing solvent; chloroform) to afford the titled Compound (j-2) as a solid (82.2 mg). Yield was 76%.

(C) Production of 3',4'-dideoxy-3'-fluorokanamycin B

The crude solid product comprising Compound (j-2) (120 mg) obtained in the step (B) above was dissolved in dry dichloromethane (3 ml), to which was added dry pyridine (0.06 ml). The mixture obtained was further admixed with trifluoromethanesulfonic anhydride (0.06 ml) at −20° C. The reaction mixture so obtained was processed in a similar manner to the step (F) of the Example 1, to afford the corresponding unstable 4'-O-trifluoromethylsulfonylated derivative of Compound (j-2) as a crude solid product (123 mg). This crude product of the 4'-O-trifluoromethylsulfonylated derivative of Compound (j-2) was dissoved in dry dimethylformamide (DMF) (2.5 ml), to which was added lithium chloride (35 mg). The mixture obtained was processed in a similar manner to the step (G) of the Example 1, to produce the corresponding 4'-epichloro derivative of Compound (j-2) as a crude solid product (105 mg). This crude product was dissolved in dioxane (2 ml), to which were added α,α'-azobis-isobutyronitrile (7 mg) and tributyltin hydride (210 mg). The mixture obtained was processed in a similar manner to the step (H) of the Example 1, to give the corresponding 4'-deoxy derivative of Compound (j-2) as a crude solid product (69 mg). This crude product was treated with metallic sodium (about 80 mg) in liquid ammonia (about 15 ml) as cooled to −50° C., to effect the removal of the benzylsulfonyl group and benzyloxycarbonyl group from said 4'-deoxy derivative. The resulting reaction product was processed in the same manner as in the step (I) of the Example 1, to afford the desired compound, 3',4'-dideoxy-3'-fluorokanamycin B as the mono-carbonate (11.0 mg). Yield was 24% based on Compound (j-2).

EXAMPLE 3

(A) Preparation of 4'',6''-O-cyclohexylidene-6'-N-methoxycarbonyl-1,3,2',3''-tetra-N-trifluoromethanesulfonyl-3'-deoxy-3'-fluorokanamycin B [Compound (e-3)]

3'-O-Benzylsulfonyl-4'-O,6'-N-carbonyl-4'',6'' O-cyclohexylidene-1,3,2',3''-tetra-N-trifluoromethanesulfonylkanamycin B [hereinafter referred to as Compound (c-3)] was treated with sodium hydroxide in anhydrous methanol to afford 4'',6''O-cyclohexylidene-3'-deoxy-3'-epi-6'-N-methoxycarbonyl-1,3,3''-tri-N-trifluoromethanesulfonyl-2',3'-(N-trifluoromethanesulfonyl)epiminokanamycin B [hereinafter referred to as Compound (d-3)] of the formula:

The Compound (d-3) (110 mg) thus obtained was dissolved in dimethylformamide (2.5 ml). The resulting solution was admixed with potassium hydrogen fluoride (40 mg) and stirred at 150° C. for 2 hours. The reaction solution was processed in a similar manner to the step (D) of the Example 1, to afford the titled Compound (e-3) as a crude solid product (72 mg).

(B) Preparation of 2''-O-acetyl-4'',6''-O-cyclohexylidene-6'-N-methoxycarbonyl-1,3,2',3''-tetra-N-trifluoromethylsulfonyl-3'-deoxy-3'-fluorokanamycin B [Compound (j-3)]

Compound (e-3) (120 mg) obtained in the step (A) was dissolved in a mixture (0.6 ml) of dry dimethylsulfoxide and pyridine (9:1), to which was added N-acetylimidazole (50 mg). The mixture was processed in a similar manner to the step (E) of Example 1, to give the titled Compound (j-3) as a solid crude product (119 mg).

(C) Preparation of 3',4'-dideoxy-3'-fluorokanamycin B

The solid crude product of Compound (j-3) (110 mg) obtained in the step (B) above was dissolved in pyridine (1.5 ml), to which was added methanesulfonyl chloride (0.0285 ml). The mixture obtained was allowed to stand at room temperature overnight (for the 4'-O-mesylation). The reaction mixture was then processed in the same manner as in the step (F) of the Example 1, to afford the corresponding 4'-O-mesyl derivative of Compound (j-3) (112 mg). The resulting 4'-O-mesyl derivative of Compound (j-3) (112 mg) was dissolved in dimethylformamide (2.5 ml), to which was added lithium chloride (30 mg), and the mixture was stirred at 70° C.

for 3 hours to effect the 4′-chlorination reaction. The reaction solution was processed in a similar manner to the step (G) of the Example 1, and the reaction product obtained was purified by silica gel column chromatography (developing solvent; chloroform-methanol (7:1)), to afford the corresponding 4′-epichloro derivative of Compound (j-3) (52 mg). This 4′-epichloro derivative was dissolved in dioxane (1.5 ml), to which were further added α,α′-azobis-isobutyronitrile (5 mg) and tributyltin hydride (100 mg). The mixture was then processed in a similar manner to the step (H) of the Example 1 to give the corresponding 4′-deoxy derivative of Compound (j-3) (31 mg). This 4′-deoxy derivative of Compound (j-3) was subjected to the deprotecting treatments in the same manner as in the step (I) of Example 1 to obtain the desired 3′,4′-dideoxy-3′-fluorokanamycin B as the mono-carbonate (6.1 mg). Yield was 12.5% based on the Compound (j-3).

EXAMPLE 4

(A) Preparation of 4″,6″-O-benzylidene-6′-N-ethoxycarbonyl-3′-deoxy-3′-fluoro-1,3,2′,3″-tetra-N-mesylkanamycin B [Compound (e-4)]

3′-O-Benzylsulfonyl-4′-O,6′-N-carbonyl-4″,6″-O-benzylidene-1,3,2′,3″-tetra-N-mesylkanamycin B [hereinafter referred to as Compound (c-4)] was treated with potassium hydroxide in anhydrous ethanol to obtain 4″,6″-O-benzylidene-3′-deoxy-3′-epi-6′-N-ethoxycarbonyl-1,3,3″-tri-N-mesyl-2′,3′-(N-mesyl)epimino-kanamycin B [hereinafter referred to as Compound (d-4)] of the formula:

The Compound (d-4) (45 mg) obtained was dissolved in dimethylformamide (1.1 ml), to which was added potassium hydrogen fluoride (18 mg). The resultant mixture was stirred at 50° C. for 2 hours for the reactions. After the completion of the reactions, the reaction solution was processed in the same manner as in the step (D) of Example 1, to afford the titled compound (e-4) as a crude solid product (28 mg).

(B) Preparation of 2″-O-acetyl-4″,6″-O-benzylidene-6′-N-ethoxycarbonyl-1,3,2′,3″-tetra-N-mesyl-3′-deoxy-3′-fluorokanamycin B [Compound (j-4)]

Compound (e-4) (120 mg) obtained in the step (A) above was dissolved in a mixture (0.6 ml) of dry dimethylsulfoxide and pyridine (9:1), to which was added N-acetylimidazole (50 mg). The reaction mixture was processed in a similar manner to the step (E) of Example 1 to produce the titled Compound (j-4) as a crude solid product (107 mg).

(C) Production of 3′,4′-dideoxy-3′-fluorokanamycin B

The crude product of Compound (j-4) (100 mg) obtained in the (B) above was dissolved in a mixture (7 ml) of dry dichloromethane and pyridine (10:1), to which was added trifluoromethanesulfonic anhydride (0.08 ml). The mixture obtained was stirred at 0° C. for 2 hours to effect the 4′-O-trifluoromethanesulfonylation. The reaction solution was admixed with water (0.03 ml) and then with chloroform (15 ml), followed by washing successively with 5% aqueous potassium hydrogen sulfate solution, with saturated aqueous sodium hydrogen carbonate solution and with water, drying over anhydrous sodium sulfate, and concentrating to dryness. The unstable 4′-O-trifluoromethylsulfonyl derivative of Compound (j-4) was thus obtained as a crude solid product (73 mg). This crude product was taken up in dry dimethylformamide (1.5 ml), to which was added lithium chloride (23 mg), and the mixture was processed in a similar manner to the step (G) of Example 1 to give the corresponding 4′-epichloro derivative of Compound (j-4) as a crude solid product (61 mg). This 4′-epichloro derivative was dissolved in dioxane (1.5 ml), to which added α,α′-azobis-isobutyronitrile (5 mg) and tributyltin hydride (120 mg). The reaction mixture was processed in a similar manner to the step (H) of Example 1 to produce the corresponding 4′-deoxy derivative of Compound (j-4) (44 mg). This 4′-deoxy derivative was subjected to the deprotecting treatments in the same manner as in the step (I) of Example 1 to afford the desired 3′,4′-dideoxy-3′-fluorokanamycin B as the mono-carbonate (7.0 mg). Yield was 13.2% based on Compound (j-4).

EXAMPLE 5

(A) Preparation of 2''-O-acetyl-4'',6''-O-cyclohexylidene-6'-N-methoxycarbonyl-4'-O-mesyl-1,3,2',3''-tetra-N-tosyl-3'-deoxy-3'-fluoro-kanamycin B [Compound (k-2)]

Compound (k-2)

Compound (j-1) (27 mg) as obtained in the step (E) of Example 1 was dissolved in dry dichloromethane (0.5 ml), to which were added dry pyridine (0.014 ml) and mesyl chloride (0.0065 ml). The mixture obtained was allowed to stand at room temperature overnight (for the 4'-O-mesylation). The reaction solution was then processed in a similar manner to the step (F) of Example 1 to afford the titled Compound (k-2) as a solid (26.5 mg).

(B) Preparation of 2''-O-acetyl-4'',6''-O-cyclohexylidene-6'-N-methoxycarbonyl-1,3,2',3''-tetra-N-tosyl-3',4'-dideoxy-4'-epi-bromo-3'-fluoro-kanamycin B [Compound (l-2)]

Compound (k-2) (30 mg) obtained in the step (A) above was dissolved in dry dimethylformamide (0.6 ml), to which was added lithium bromide (19 mg). The mixture obtained was allowed to stand at 50° C. overnight (for the 4'-bromination). The reaction solution was poured into water (10 mg) to precipitate a solid. The solid precipitate as recovered was processed in a similar manner to the step (G) of Example 1 and purified by silica gel chromatography [developing solvent: chloroform-acetone (2:1)], to give the titled Compound (l-2) as a crude solid product (17.3 mg).

(C) Preparation of 2''-O-acetyl-4'',6''-O-cyclohexylidene-6'-N-methoxycarbonyl-1,3,2',3''-tetra-N-tosyl-3',4'-dideoxy-3'-fluorokanamycin B [Compound (m-1)].

Compound (l-2) (35 mg as the crude product) obtained in the above step (B) was dissolved in dioxane (1 ml), to which were added α,α'-azobis-isobutyronitrile (2.3 mg) and tributyltin hydride (40 mg). The reaction mixture was processed in the same manner as in the step (H) of Example 1 to obtain the titled Compound (m-1) as a colorless solid (14.3 mg). Yield is 43% based on Compound (k-2).

(D) Production of 3',4'-dideoxy-3'-fluorokanamycin B

Compound (m-1) as obtained in the step (C) above was subjected to the deprotection treatments in the same manner as in the step (I) of Example 1 to yield the title Compound.

EXAMPLE 6

(A) Preparation of 2''-O-acetyl-4'',6''-O-cyclohexylidene-6'-N-methoxycarbonyl-4'-O-tosyl-1,3,2',3''-tetra-N-tosyl-3'-deoxy-3'-fluorokanamycin B [Compound (k-3)]

Compound (j-1) (26.5 mg) as obtained in the step (E) of Example 1 was dissolved in dry pyridine (0.5 ml), to which was added tosyl chloride (19.7 mg). The mixture obtained was allowed to stand at 50° C. overnight (for the 4'-O-tosylation). The reaction solution was processed in the same manner as in the step (F) of Example 1 to afford the titled Compound (k-3) as a solid product (27.0 mg).

(B) Preparation of 2''-O-acetyl-4'',6''-O-cyclohexylidene-6'-N-methoxycarbonyl-1,3,2',3''-tetra-N-tosyl-3',4'-dideoxy-4'-epi-iodo-3'-fluorokanamycin B [Compound (l-3)]

Compound (k-3) (35 mg) obtained in the step (A) above was dissolved in dry dimethylformamide (DMF) (0.6 ml). Sodium iodide (100 mg) was added to the resulting solution, followed by stirring at 50° C. for 10 hours to effect the 4'-iodination. The reaction solution was poured into water (10 ml), and a solid precipitate as formed was recovered and processed in a similar manner to the step (G) of Example 1 and purified by silica gel column chromatography [developing solvent: chloroform-acetone (2:1)], to produce the titled Compound (l-3) as a crude solid product (13.9 mg).

(C) Preparation of 2''-O-acetyl-4'',6''-O-cyclohexylidene-6'-N-methoxycarbonyl-1,3,2',3''-tetra-N-tosyl-3',4'-dideoxy-3'-fluorokanamycin B [Compound (m-1)]

Compound (l-3) (40 mg) obtained as the crude product in the step (B) above was dissolved in dioxane (1 ml). To the resulting solution were added α,α'-azobisisobutyronitrile (2.3 mg) and tributyltin hydride (35 mg). The reaction mixture was processed in the same manner as in the step (H) of Example 1 to afford the titled Compound (m-1) as a solid product (16.4 mg). Yield was 45% based on Compound (k-3).

(D) Production of 3',4'-dideoxy-3'-fluorokanamycin B

Compound (m-1) as obtained in the step (C) above was subjected to the deprotecting treatments in the same manner as in the step (I) of Example 1, to give the titled Compound.

What we claim is:

1. 3',4'-Dideoxy-3'-fluorokanamycin B of the formula (I)

and a pharmaceutically acceptable acid addition salt thereof.

2. An antibacterial composition comprising an antibacterially effective amount of 3',4'-dideoxy-3'-fluorokanamycin B as defined in claim 1, or a pharmaceutically acceptable acid addition salt thereof, as the active ingredient, in association with a pharmaceutically acceptable solid or liquid carrier for the active ingredient.

3. A process for preparing 3',4'-dideoxy-3'-fluorokanamycin B as defined in claim 1 and represented by the formula (I)

which comprises the steps of:
(i) reacting an N,O-protected 3'-O-sulfonyl-6'-N,4'-O-carbonyl-kanamycin B derivative of the formula:

(V)

wherein B is an amino-protecting group selected from an alkylsulfonyl group, an aralkylsulfonyl group and an arylsulfonyl group; X and Y are each a hydrogen atom or a mono-valent hydroxyl-protecting group, or X and Y as taken together form a di-valent hydroxyl-protecting group; Q is an alkylsulfonyl group, an aralkylsulfonyl group or an arylsulfonyl group same as the group B; Z is an alkylsulfonyl group, an aralkylsulfonyl group or an arylsulfonyl group which is the same as or different from the group Q, and V' is a hydroxyl-protecting group or a hydrogen atom, with an alkali metal hydroxide in the presence of methanol, ethanol or benzyl alcohol, to produce an N,O-protected 3'-deoxy-3'-epi-2',3'-epimino-6'-N-alkoxy- or aralkyloxy-carbonylkanamycin B derivative of the formula:

(VI)

wherein B, X, Y, Q and V' are as defined above; A' is an amino-protecting group selected from methoxycarbonyl group, ethoxycarbonyl group and benzyloxycarbonyl group, (ii) reacting the resulting compound of the formula (VI) with an alkali metal hydrogen difluoride of the formula:

MeHF$_2$ (VII)

wherein Me is an alkali metal atom, in an organic solvent under heating, to produce a 3'-deoxy-3'-fluorokanamycin B derivative of the formula:

(VIII)

wherein A' is the amino-protecting group selected from methoxycarbonyl group, ethoxycarbonyl group and benzyloxycarbonyl group; B is an amino-protecting group as defined above; V', X and Y are as defined above, (iii) protecting the 2''-hydroxyl group of the compound of the formula (VIII) with a hydroxyl-protecting group, when the compound (VIII) is containing the hydrogen atom for the symbol V'.

(iv) reacting the compound of the formula (VIII) where V' is a hydroxyl-protecting group, with a sulfonic acid halide of the formula:

RSO$_2$D' (IX)

wherein R is an alkyl group, an aralkyl group or an aryl group and D' is a chlorine, bromine or iodine atom, or with a corresponding sulfonic anhydride of the formula:

(RSO$_2$)$_2$O (IX')

wherein R is as defined above, to produce a 3'-deoxy-3'-fluoro-4'-O-sulfonylkanamycin B derivative of the formula:

(II')

wherein R is an alkyl group, an aralkyl group or an aryl group; A' is an amino-protecting group selected from methoxycarbonyl group, ethoxycarbonyl group and benzyloxycarbonyl group; B is an amino-protecting group selected from an alkylsulfonyl group, an aralkylsulfonyl group and an arylsulfonyl group; X and Y are each a hydrogen atom or a mono-valent hydroxyl-protecting group, or X and Y as taken together form a di-valent hydroxyl-protecting group; Q is an alkylsulfonyl group, an aralkylsulfonyl group or an arylsulfonyl group which is the same as the group B; V is a hydroxyl-protecting group, (v) reacting the compound of the formula (II) with a metal halide of the formula:

MD (III)

wherein M is a metal and D is a chlorine, bromine or iodine atom, to produce a 4'-halogenated product of the formula:

(IV')

wherein A', B, Q, V, X, Y and D are as defined above, (vi) removing the 4'-halo group (D) from the compound (IV') by reduction and thereby to produce a corresponding N,O-protected 3',4'-dideoxy-3'-fluorokanamycin B derivative, and (vii) removing the remaining amino-protecting groups (A', B, Q), as well as the remaining hydroxyl-protecting groups (V, X, Y) from the resultant N,O-protected 3',4'-dideoxy-3'-fluorokanamycin B derivative.

* * * * *